United States Patent [19]

Kao

[11] 4,100,188

[45] Jul. 11, 1978

[54] CHEMICAL PROCESS

[75] Inventor: James T. F. Kao, Baton Rouge, La.

[73] Assignee: Ethyl Corporation, Richmond, Va.

[21] Appl. No.: 248,053

[22] Filed: Apr. 27, 1972

[51] Int. Cl.² ............................................. C07C 59/12
[52] U.S. Cl. ................................................ 260/535 P
[58] Field of Search ...................................... 260/535 P

[56] References Cited

U.S. PATENT DOCUMENTS

| | | | |
|---|---|---|---|
| 3,635,830 | 1/1972 | Lamberti | 252/152 |
| 3,692,685 | 9/1972 | Lamberti | 260/535 P |

*Primary Examiner*—Paul J. Killos
*Attorney, Agent, or Firm*—Donald L. Johnson; John F. Sieberth; Shelton B. McAnelly

[57] ABSTRACT

It is disclosed that water soluble salts of carboxyalkoxy succinic acids are obtained in solid form by crystallization from mixed solvent systems wherein the solvents are water plus a lower alkanol having up to about six carbon atoms per molecule. A particularly preferred alkanol is methanol. The selective production of salts containing various amounts of water of hydration is possible by controlling the ratio of water to alcohol.

16 Claims, 1 Drawing Figure

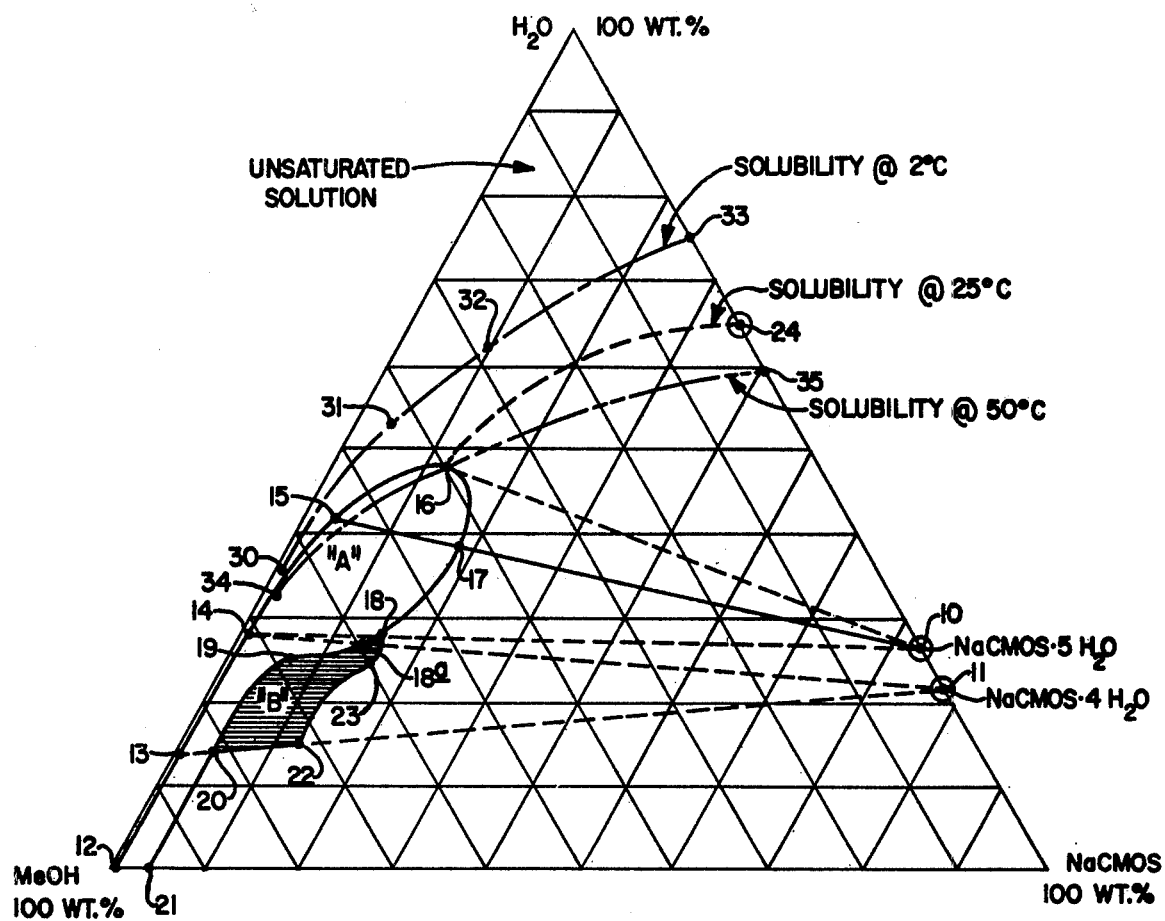

CHEMICAL PROCESS

BACKGROUND OF THE INVENTION

1. Field of the Invention

This invention relates in general to the preparation of salts of carboxyalkoxy succinic acid and in particular to the preparation of said salts in solid particulate form.

2. Description of the Prior Art

It is known that salts of carboxyalkoxy succinic acid are useful detergent components, particularly valuable as builders in detergent formulations.

Introduction

Generally, the salts of the present invention useful as builders are water soluble salts of acids which have the formula:

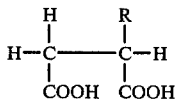

wherein R is a carboxyalkoxy radical (—OR'COOH) having from 2 to about 7 carbon atoms total, R' preferably being a "divalent, straight chain alkyl" structure $[—(CH_2)_n—]$ where $n$ is 1-6. Examples of such acids are α-carboxymethoxy succinic acid, α-(1-carboxybutoxy) succinic acid, α-(2-methyl-3-carboxybutoxy) succinic acid, α-(1-carboxyhexoxy) succinic acid, α-carboxyisobutoxy succinic acid, and the like. A preferred acid has been found to be the above mentioned α-carboxymethoxy succinic acid because the alkali metal and other water soluble salts thereof are readily produced at low cost and are effective and useful detergent builders.

Typical useful water soluble salts of α-carboxymethoxy succinic acid are the alkali metal, the ammonium and the lower alkanol ammonium salts having from 2 to about 6 carbon atoms in the alkanol structure such as sodium salts, potassium salts, ammonium salts, triethanol ammonium salts, diethanol ammonium salts, monoethanol ammonium salts, monoisopropanol ammonium salts, mono-n-butanol ammonium salts, and the like and mixtures of two or more thereof.

Preferred salts are the sodium, potassium and ammonium salts, with the sodium salts being particularly preferred because of low cost, effectiveness and ease of production.

The builders of this invention can be used to advantage with a wide variety of detergent actives or surfactants, including those known in the art as anionic, cationic, nonionic, ampholytic, ampholotic and zwitterionic detergents as well as any suitable mixture of such detergents. Included also are soaps such as those of natural or synthetic origin coconut and tallow range soaps of straight chain or branched chain carbon skeleton structures.

Typical detergent mixtures contain the builders of this invention with or without one or more other builders such as salts of other polycarboxylic acids, typically oxydisuccinic acid, nitrilotriacetic acid, phosphoric acid, tartaric acid, tetrahydrofuran tetracarboxylic acid, citric acid; plus one or more of the conventional actives such as alkyl benzene sulfonates, olefin sulfonates, sulphobetaines, alkanol sulfates, alkanol alkoxy sulfates, amides, amine oxides and the like. When the resultant washing compositions are used in aqueous washing systems, the cleaning power of the formulation is enhanced in much the same way as when the commonly used alkali metal polyphosphate salt builders are employed as the only builders. Yet the present builder systems do not contribute to or magnify the eutrophication problems characteristic of phosphorus-containing builders. The builders of the present invention are generally used in formulations containing other agents such as abrasives, dyes, perfumes, anti-redeposition agents, pH modifiers, inorganic salts such as sodium chloride, lime-soap dispersants, brighteners, bacteriostats, water hardness additives, and the like.

It is known that α-carboxymethoxy succinic acid salt is produced by reacting salts of glycolic acid and maleic acid in an aqueous medium in the presence of enough zinc or alkaline earth metal hydroxide typically, calcium hydroxide, to produce a salt system having a pH of at least about 8 and preferably higher than about 11 when measured at 25° C. The reaction is preferably conducted at reflux temperature for from about 1 to about 6 hours. Typically, the salt system thus obtained is reacted with an alkali metal carbonate such as sodium or potassium carbonate at a moderate temperature of about 60° C, for example, and cooled to room temperature of about 25° to 30° C following which suspended zinc or alkaline earth metal carbonate is filtered off yielding a water solution containing trisodium carboxymethoxy succinate or tripotassium carboxymethoxy succinate. Such solutions can also be produced in other ways such as by converting the zinc or alkaline earth metal salt into acid and reacting the α-carboxyalkoxy succinic acid with an organic or an inorganic base to produce other salts typified herein such as the ammonium or alkanol ammonium salts.

Recovery of the water soluble carboxymethoxy succinic acid salts in particulate form from the aqueous solutions containing them is difficult. The usual or frequent result of attempting to recover the solids from the solution by simple procedure as for example by ordinary drum drying or spray drying to remove water is the production of an impure, sticky material which is contaminated with undesirably large quantities of residual reactants and by-product materials. Furthermore, the usual product obtained by such ordinary evaporation is hygroscopic giving various problems with regard to the storage and handling of the salt itself as well as of particulate materials such as detergents containing the salt product.

SUMMARY OF THE INVENTION

Since it is desirable to be able to produce a pure succinic acid salt product substantially free of contamination by residual reactants and by-products and which is not hygroscopic in storage and handling, an object of the present invention is to provide an improved process for the purification and recovery of water soluble salts of carboxyalkoxy succinic acid from aqueous solutions. Another object of the present invention is to provide a process for producing water soluble carboxyalkoxy succinic acid salts which are not hygroscopic.

Another object of the present invention is to provide a process for producing purified particulate sodium carboxymethoxy succinates in high yield and purity.

Other and further objects and features of the present invention will become apparent upon careful consideration of the following detailed discussion and the accompanying drawing, the single FIGURE of which shows a ternary diagram illustrating the properties of various compositions useful to illustrate the method of operation of the present purification and recovery process.

It has been discovered that water soluble hydrate salts of carboxyalkoxy succinic acid, especially trisodium carboxymethoxy succinate tetra- and penta-hydrate and can be produced in excellent purity and in a moisture stable form by precipitation from certain mixed solvent systems. Surprisingly, the proportions of solvents and solute influence results to a marked extent and are critical in certain respects to provide the most highly desired results. Usually for the most highly desired results it is desired to avoid proportions in which the mother liquor enters a "morass" region of composition or proportions either before or after precipitation because once this happens, the system usually becomes difficult to handle unless it is redissolved with solvent. Data for various proportions of various materials and for various temperatures have been plotted in a ternary diagram to show graphically the desired and the undesired regions of operation.

By selection of conditions and processing as taught herein one readily obtains a highly pure product which is not hygroscopic and is free of caking tendencies. Furthermore, with this process one can select various hydrated forms of the product. Thus, for example, it is possible to produce a product which is essentially pure pentahydrate or which is essentially pure tetrahydrate or which is a selected proportion mixture of the two. The terms tetra- and penta-hydrate are used to define crystallization forms in which the ratio of the number of molecules of water of hydration per molecule of "anhydrous" carboxymethoxy succinic acid salt is 4 to 1 or 5 to 1, respectively. Not only does the process provide for selectivity with regard to the hydration ratio but intermediate product mixtures are also selectable having intermediate "average" fractional ratios such as 4.5 to 1, 4.2 to 1, 4.7 to 1, etc.

The ability to controllably produce such mixtures is a useful feature of the process of the present invention. Like the tetra- and penta-hydrates produced by the present process, the intermediate mixtures are also stable with regard to hygroscopic properties; that is, unless subjected to extremes of temperature and/or moisture, they do not pick-up or lose water or change from one hydrate form to another. Thus, the products of the process are suitably stored at ordinary room temperatures or at outdoor temperatures even in bulk in covered bins, are withdrawn from the bins and blended with other particulate detergent components, are packaged in paper or cardboard containers and are used from such packages without problems of caking or "drying out" in storage or handling.

The process of the present invention is based on a selection and control of proportions of systems that contain two solvents and one principal solute. Impurity solutes are generally present also in quantities which are, proportionally speaking, only a small percentage of the amount of the principal solute; however, it is characteristic of the present process, based on crystallization, that the impurities remain almost entirely in either or both of the solvents and that the principal solute crystallization product is virtually free of the impurities. The impurities are, generally speaking, residual reactants or by-products and are usually desirably recovered from the solvents and recycled to the processing operations.

Thus, the present process involves the formation and manipulations of systems containing two types of solvents and a principal solute from which recovery of the principal solute in particulate or crystalline form is desired. Usually the systems consist essentially of the solvents and the principal solute and may contain in addition minor proportions of one or more impurity solvents which are residual reactant or intermediate materials.

In accordance with the present process an alkali metal ammonium or amine salt of carboxyalkoxy succinic acid is recovered from an aqueous solution thereof by combining said solution with lower alkanol having from 1 to about 3 carbon atoms per molecule to form a system consisting essentially of (1) water, (2) alkanol, and (3) said salt. Preferred systems so formed contain from about one-half to about 10 parts by weight of alcohol per part of aqueous salt solution, the weight ratio of salt (anhydrous basis) to water being from about 1:10 to about 1:1 parts by weight, said system containing greater than a saturation amount of salt. Such systems usually contain minor proportions of impurities such as sodium maleate, glycolate, or fumarate.

The system described can be formed in any of several ways. In the first place, the components can be combined in various sequences using individual components or sub-combinations and the solvent content can be adjusted by distillation. A system thus formed is then allowed to undergo precipitation of salt, which precipitate is recovered by any suitable processing, typically filtration or centrifuging. Temperatures are from about 0° to about 120° C, preferably from about 20° to about 50° C, particularly about 20° to about 35° C, typically 25° C. Preferably the proportions of alcohol, water and salt are such that the mother liquor present in the system avoids the region "B" of the FIGURE; viz, the area bounded by the lines connecting 18, 18-a, 19, 20, 22, 23 and 18.

In a preferred aspect of the present invention, the system proportions fall within the region "A" of the FIGURE in the area bounded by the lines connecting 12, 13, 14, 15, 16, 17, 18, 18-a, 19, 20, 21 and 12, particularly where the system has at least 10 percent by weight of water.

In a preferred aspect, the water content of the alkanol-water-salt systems formed in the present process is from about 15 percent to about 50 percent by weight.

In a preferred aspect of the present process the system is formed by adding the alkanol to an aqueous solution of the salt.

In a preferred aspect of the process of the present invention the system is formed by adding an aqueous solution of the salt to the alkanol.

In a preferred aspect of the process of the present invention the weight ratio of alkanol to the balance of the system is from about 1:1 to about 4:1.

In a preferred aspect of the process of the present invention the weight ratio of alkanol to the balance of the system is from about 1.5:1 to about 2.5:1, particularly about 2:1.

In a preferred aspect of the present process, the system is formed at a temperature of from about 20° to about 50° C and the system temperature is maintained in the specified region during precipitation of trisodium carboxymethoxy succinate.

In a preferred aspect of the present process, the salt in the system formed is an alkali metal salt, especially a sodium salt of carboxymethoxy succinic acid, and the amount of said salt is from about 10 to about 40 percent by weight (anhydrous basis) based on the water present in the system.

In a preferred aspect of the present process the salt in the system is alkali metal, e.g. sodium, salt of carboxymethoxy succinic acid, and the amount of said salt (anhydrous basis) is from about 2 percent to about 20 percent by weight of the total system.

A preferred process in accordance with the present invention recovers a sodium salt of carboxymethoxy succinic acid from an aqueous solution thereof by forming at a temperature of from about 0 to about 100° C a system consisting essentially of (1) water, (2) methanol, and (3) said salt in proportions of from about 3.5:1 to about 4:1 parts by weight of alcohol per part of water and salt, the percentage of said salt (anhydrous basis) based on the water of said system being from about 15 to about 25 percent by weight, said system containing at least a saturation amount of said salt. The system thus formed in the foregoing proportions usually contains minor amounts of formate, maleate and glycolate impurities. Preferably, the system is agitated vigorously at first to provide good contact and then is agitated gently thereafter to form a precipitate hydrate sodium salt of carboxymethoxy succinic acid, following which the hydrate salt precipitate is recovered from the system. The present process is further characterized in that the proportions of alcohol, water and salt are such that the mother liquor does not enter the region "B" of the FIGURE within the area bounded by the lines shown connecting points 18, 18-a, 19, 20, 22, 23 and 18 before or during precipitation of said salt.

Typical salts are:
sodium carboxymethoxy succinate
potassium carboxymethoxy succinate
ammonium carboxymethoxy succinate
monoethanolammonium carboxymethoxy succinate
diethanolammonium carboxymethoxy succinate
triethanolammonium carboxymethoxy succinate
sodium carboxyethoxy succinate
potassium carboxyethoxy succinate
ammonium carboxyethoxy succinate
monoethanolammonium carboxyethoxy succinate
diethanolammonium carboxyethoxy succinate
triethanolammonium carboxyethoxy succinate
sodium carboxypropoxy succinate
sodium carboxybutoxy succinate
sodium carboxypentoxy succinate
sodium carboxyhexoxy succinate The foregoing salts exist in various hydrated forms with different amounts (mols) of water of hydration per mol of hydrated salt.

Typical alkanols are methanol, ethanol, isopropanol and normal propanol. Preferred is methanol because of its outstanding solubility characteristics, its low cost and ready availability.

Numerous detergent compounds useful with the builders produced in accordance with the present process are described in "Surface Active Agents" by Schwartz and Perry, Interscience Publishers, Inc., New York 1949.

The present process utilizes to advantage the properties of ternary systems of water, lower alkanol having from 1 to about 3 carbon atoms per molecule and salts as defined wherein a typical aqueous solution of sodium carboxymethoxy succinic acid containing from about 10 percent to about 40 percent of said salt by weight (anhydrous basis) is combined with the alkanol to form a system which is supersaturated with respect to said salt so that precipitation readily takes place. The hydrated salt precipitate formed from such a system is readily recovered by conventional solids recovery operations such as filtration or centrifuging and is then dried to remove surface moisture to produce a free-flowing particulate solid material which has 4 or 5 molecules of water of hydration per molecule of salt or a mixture of the tetrahydrate and the pentahydrate and which is substantially water stable; that is, it does not lose or pick up water on standing under normal storage conditions, and it has a high purity.

Careful attention to proportions in the mother liquor as well as the initial systems is necessary. Otherwise one occasionally or frequently encounters seemingly mysteriously systems which have a molasses-like consistency or viscosity. The salt is not easily separated from such a system using conventional filtration or centrifuging operations. An area "B" of undesired proportions from this viewpoint is identified in the FIGURE. The area "B" is that of the initial system proportions overall or the proportions of the mother liquor at any point in time as a crystallization proceeds in batch or continuous operation. Once the mother liquor of the system enters this region "B", recovery of the salt in solid particulate form and in high purity is difficult perhaps even impossible. Thus, an important aspect of the process of the present invention is the avoidance of an undesired region of proportions in systems of the foregoing type.

The undesired region of compositions to be avoided can be encountered in several ways. In the first place it can be produced at the outset of formation of the system of salt water and alkanol in those circumstances where one combines the components in such proportions that the total system falls within the region described. In addition to this, the undesired region may be entered by the mother liquor subsequent to the formation of a suitable initial system as a result of the precipitation of salt. In this latter situation, it is observed that precipitation appears to progress satisfactorily but only up to a point; however, the recovery of salt from such a system is difficult.

The foregoing general discussion may be explained more fully with reference to the FIGURE which shows a weight basis ternary diagram indicating properties of various systems according to the typical present invention. Except as otherwise indicated this FIGURE is for a typical system based on methanol, on sodium salts of carboxymethoxy succinic acid and is at 25° C. Other representations are made for other temperatures. As is customary in ternary diagrams the apexes indicate respectively 100 percent water at the top, viz, 100 percent (anhydrous) sodium salt of carboxymethoxy succinic acid at the lower right and 100 percent methyl alcohol at the lower left. A "dry" solid particulate pentahydrate of the sodium salt of carboxymethoxy succinic acid is indicated on the salt-water binary axis at point 10. Similarly, a "dry" tetrahydrate of the sodium salt of carboxymethoxy succinic acid is indicated on the salt-water binary axis at point 11.

A region of preferred operations in many cases is the kidney-shaped area indicated by the letter "A" identified by the lines connecting points 12, 13, 14, 15, 16, 17, 18, 18-a, 19, 20, 21 and back to point 12. An undesired region is indicated by the area "B" identified by the lines connecting points 18, 18-a, 19, 20, 22, 23 and back to point 18. In general, the region on and "below" the line 12, 13, 14, 15, 16 and 24 in the FIGURE represents saturated or supersaturated systems from which precipitation of sodium salts of carboxymethoxy succinic acid occurs readily. Systems in the region above the foregoing line 12, 13, 14, 15, 16 and the extension to 24 are unsaturated solutions from which precipitation will not occur until the solutions are rendered more concentrated in salt, typically by the evaporation removal of some of the solvent.

The ability to selectively produce the different hydrated forms of salt is indicated on the FIGURE by the dotted lines 10-14, 10-16, 11-14 and 11-13. Generally speaking, crystallization within the region 14, 15, 16, 10 and back to 14 produces the pentahydrate sodium salt of carboxymethoxy succinic acid, while crystallization within the region 14, 11, 22, 20, 13 and back to 14 produces the tetrahydrate form except for region "B". Compositions along the typical intermediate line 15, 17, 10 represents particularly desirable compositions for the formation of the pentahydrate at high crystallization rate and in excellent selectivity. The region within 14, 18-a, 19, 20, 13 and back to 14 represents a particularly desired region for initial system compositions when production of the tetrahydrate is desired. In this connection, it is pointed out that initial system compositions within the region 14, 18-a, 19, 20, 13 and 14 generally can approach quite closely to the undesired region "B" without difficulty because as crystallization proceeds removing salt from solution, the actual mother liquor composition moves generally to the left away from the salt apex. On the other hand, it is important to observe that initial compositions out of region "B" to the right of the line 22, 23, 18 can be unsuitable because as the crystallization progresses, the mother liquor composition moves toward the left and can enter the undesired region "B".

The dash-dot line 30, 31, 32 and 33 of the FIGURE shows the saturation line for methanol-water-sodium salt of carboxymethoxy succinic acid systems at 2° C. Beyond point 30, toward the alcohol apex at the lower left, the properties of the systems at 2° C are very close to those at 25° C. Line 34-35 is for 50° C.

The properties of systems of potassium salts of carboxymethoxy succinic acid are generally similar to those of the trisodium systems; however, the solubility of the potassium salts is higher than that of the sodium salts so that one usually prefers systems which are more concentrated in salt than the sodium salt systems. The ammonium, quarternary ammonium, alkanol ammonium, miscellaneous amine and amide systems are frequently formed by reacting the substituted succinic acid with ammonia as the appropriate base, or by other suitable well known reactions.

EXAMPLE I 20 lbs of an aqueous solution containing 19.2 wt percent of the sodium salt of carboxymethoxy succinic acid (sodium CMOS) was added to 80 lbs of methanol over a period of 10 minutes at room temperature with agitation. The slurry was stirred overnight and then filtered. The wet cake was dried to a content of 22.6 percent water (21.8 percent water for tetrahydrate salt). X-ray diffraction showed the product to be tetrahydrate salt. NMR analysis showed pure sodium CMOS with no detectable impurities. 4.6 pounds of "dried" solids was obtained which corresponded to a 93.5 percent recovery based on the starting sodium CMOS.

EXAMPLE II 100 grams of methanol was added with agitation to 100 grams of a solution of sodium CMOS containing 19.1 wt percent sodium CMOS at room temperature. A clear solution resulted initially after completion of the addition. The solution was stirred for a period of two hours. Solid sodium CMOS crystallized out gradually. The slurry was centrifuged to separate the solids from the solvent. The wet solids were dried. 20.3 grams of crystalline product was recovered containing 26.7 percent water (25.9 percent water for pentahydrate salt). X-ray diffraction confirmed the crystalline structure as pentahydrate salt. The recovery was 78 percent based on the sodium CMOS.

EXAMPLE III

Example II was repeated, however the weight ratio of methanol to the sodium CMOS solution was 1.5:1. The recovery was 88 percent. By X-ray diffraction analysis the product was shown to be a mixture of pentahydrate and tetrahydrate salts.

EXAMPLE IV 100 grams methanol was added to 100 grams of a 33.6 percent sodium CMOS aqueous solution as in Example II. A thick slurry was obtained. After separation and drying, the recovery was over 89 percent.

EXAMPLE V

To 100 grams of a 16.8 percent of sodium CMOS solution, 250 grams of methanol was added and a product separated as in Example II. The product was washed with 50 ml of a methanol-water solution containing 25 wt percent methanol. The product purity was checked by NMR before and after methanol precipitation and washing. The analyses in normalized mol percent are as follows:

| Component | Mol Percent Before | Mol Percent After |
| --- | --- | --- |
| Sodium CMOS | 82 | 100 |
| Sodium Fumarate | 4 | 0 |
| Sodium Glycolate | 4 | 0 |
| Sodium Maleate | 7 | 0 |
| Other Organic Impurities | 3 | 0 |

EXAMPLE VI 100 grams of an aqueous solution containing 18.3 percent sodium CMOS was added to 250 grams of methanol as in Example I. A sticky, taffy-like material formed. The system could not be agitated. It was not possible to separate sodium CMOS from the system by filtration.

EXAMPLE VII 200 grams of an aqueous solution containing 11.35 percent sodium CMOS was concentrated to 52 grams by evaporation of water and 130 grams of methanol was added. A sticky and gummy material was formed as in Example VI. It was not possible to separate sodium CMOS from the system by filtration.

EXAMPLE VIII

Procedures similar to Examples I and II were followed to define the curves shown in the FIGURE for sodium CMOS for various compositions at 2° C, 25° C and 50° C.

EXAMPLE IX

Calcium CMOS was prepared by reacting salts of glycolic acid and maleic acid in an aqueous medium in the presence of Ca(OH)$_2$ to produce a salt system having a pH of at least 8 when measured at 25° C. The reaction was at reflux temperature.

The product was as follows:

| Component (as acid) | Calcium Salts (mol %) |
|---|---|
| Carboxymethoxy Succinic Acid | 74 |
| Maleic Acid | 8 |
| Glycolic Acid | 11 |
| Glycolic Acid, Methyl Ether | 3 |
| Fumaric Acid | 3 |
| Methanol | 1 |
| | 100 |

The calcium product was reacted with potassium carbonate at about 60° and cooled to room temperature. Suspended calcium carbonate was then filtered yielding an aqueous solution as follows:

| Component (as Acid) | Potassium Salts (Wt % in Solution) |
|---|---|
| Carboxymethoxy Succinic Acid | 27.5 |
| Maleic Acid | 0.6 |
| Glycolic Acid | 1.2 |
| Glycolic Acid, Methyl Ether | 0.5 |
| Fumaric Acid | 1.7 |
| Methanol | Trace |

Water was evaporated from the potassium salt solution until the concentration of potassium CMOS was 72.5 wt percent. The resulting solution was mixed with methanol (5.5 parts methanol per part of solution). Potassium CMOS precipitated out and was recovered.

EXAMPLE X

To 100 grams of an aqueous solution containing 8.1 percent by weight of carboxymethoxy succinic acid was added 3.0 grams of ammonium carbonate producing a system having a pH of 9.0.

Then 1150 grams of methanol was added to the salt solution. A precipitate formed. 4.0 grams of the ammonium salt of carboxymethoxy succinic acid was recovered.

What is claimed is:

1. A process for recovering an alkali metal, ammonium or amine salt of carboxyalkoxy succinic acid from an aqueous solution thereof which comprises combining said solution with lower alkanol having from 1 to about 3 carbon atoms per molecule to form a system consisting essentially of (1) water, (2) alkanol, and (3) said salt, said system containing from about one-half to about 10 parts by weight of alcohol per part of aqueous salt solution, the weight ratio of salt to water being from about 1:10 to about 1:1, said system containing greater than a saturation amount of salt, and recovering a precipitate of salt from said system.

2. The process of claim 1 further characterized in that the mother liquor present in the system avoids the region "B" of the FIGURE.

3. The process of claim 1 wherein the proportions of water alcohol and salt fall within the region "A" of the FIGURE.

4. The process of claim 1 wherein the water content of the system is from about 15 percent to about 50 percent by weight.

5. A process in accordance with claim 1 wherein the system is formed by adding the alkanol to an aqueous solution of the salt.

6. A process in accordance with claim 1 wherein the system is formed by adding an aqueous solution of the salt to the alkanol.

7. The process of claim 1 wherein the weight ratio of alkanol to the balance of the system is from about 1:1 to about 4:1.

8. The process of claim 1 wherein the weight ratio of ankanol to the balance of the system is from about 1.5:1 to about 2.5:1.

9. The process of claim 1 wherein the weight ratio of alkanol to the balance of the system is about 2:1.

10. The process of claim 1 wherein the temperature is from about 20 to about 50° C.

11. The process of claim 1 wherein the salt is an alkali metal salt of carboxymethoxy succinic acid and the amount of said salt is from about 10 to about 40 percent by weight based on the water present.

12. The process of claim 1 wherein the salt is an alkali metal salt of carboxymethoxy succinic acid and the amount of said salt is from about 2 percent to about 20 percent by weight of the total system.

13. The process of claim 1 wherein the salt is a sodium salt of carboxymethoxy succinic acid and the amount of said salt is from about 10 to about 40 percent by weight based on the water present.

14. The process of claim 1 wherein the salt is a sodium salt of carboxymethoxy succinic acid and the amount of said salt is from about 2 percent to about 20 percent by weight of the total system.

15. A process for recovering the sodium salt of carboxymethoxy succinic acid from an aqueous solution thereof which comprises forming at a temperature of from about 0° to about 100° C a system consisting essentially of (1) water, (2) methanol, and (3) said salt, in proportions of from about 3.5:1 to about 4:1 parts by weight of alcohol per part of water and salt, the percentage of said salt based on the water being from about 15 to about 25 percent by weight, said system containing at least a saturation amount of salt, and recovering a precipitate of said salt, the foregoing process further characterized in that the liquor of the system does not enter the region "B" of the FIGURE before or during precipitation of said salt.

16. A process for the production of a water soluble sodium-, potassium- or ammonium salt of a carboxyalkoxy succinic acid of the general formula

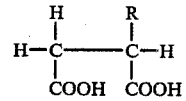

wherein R is a carboxyalkoxy radical (—OR'COOH) having from 2 to about 7 carbon atoms total, R' is a divalent, straight chain alkyl structure [—(CH$_2$)$_n$—] where $n$ is 1-6, in particulate form from an aqueous solution of the salt, characterized in that the solution is mixed with methanol in proportions of ½ to 10 parts per weight per part of the aqueous solution.

* * * * *